United States Patent [19]

Marchi et al.

[11] Patent Number: 5,639,744
[45] Date of Patent: Jun. 17, 1997

[54] BILE ACIDS DERIVATIVES USEFUL IN THE THERAPY OF THE BILIARY CALCULOSIS FROM CHOLESTEROL AND OF THE PATHOLOGIES CAUSED BY CHOLESTASIS

[75] Inventors: Egidio Marchi; Maria Rita Milani; Silvano Piani; Aldo Roda; Gianfranco Cainelli, all of Bologna, Italy

[73] Assignee: Alfa Wassermann S.p.A., Alanno, Italy

[21] Appl. No.: 416,155

[22] Filed: Apr. 4, 1995

[30] Foreign Application Priority Data

Apr. 6, 1994 [IT] Italy .................. BO94A0146

[51] Int. Cl.⁶ .................. A61K 31/58; C07J 43/00
[52] U.S. Cl. .................. 514/176; 540/110
[58] Field of Search .................. 540/110; 514/176

*Primary Examiner*—Kimberly J. Prior
*Attorney, Agent, or Firm*—Bucknam and Archer

[57] ABSTRACT

An amide of formula

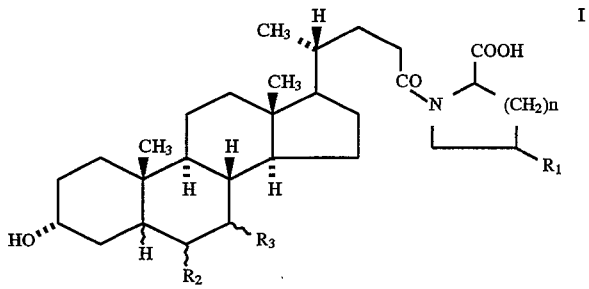

and its pharmacologically acceptable organic or inorganic salt shows a metabolic stability, both enteric and hepatic, greater than that of the corresponding bile acids conjugated with glycine or taurine physiologically present in the enterohepatic circulation. The pharmacological activity of the compounds of formula I or their pharmacologically acceptable organic or inorganic salt makes the use effective for the therapy of biliary calculosis from cholesterol and in every pathology caused by cholestasis like chronic hepatitis from cholestasis, primitive biliary cirrhosis and juvenile hepatopathy associated with cystic fibrosis.

15 Claims, 1 Drawing Sheet

BILE ACIDS DERIVATIVES USEFUL IN THE THERAPY OF THE BILIARY CALCULOSIS FROM CHOLESTEROL AND OF THE PATHOLOGIES CAUSED BY CHOLESTASIS

BACKGROUND OF THE INVENTION

The main metabolites of cholesterol are the bile acids which make easier its elimination through the feces by forming micelles, as reported by Small D. M. in *The bile acids—Chemistry, Physiology and Metabolism*, Vol. 1 Nair P. P. and Kritchevsky D. Eds., Plenum Press, N.Y., 249–355, (1971). During the enterohepatic circulation, a process of conjugation takes place in the liver between glycine and taurine and the free bile acids are produced by cholesterol before their secretion into the ductus bilifer and the duodenum. The bile acids take part in the mechanism of absorption of fats and other lipids into the intestinal lumen by forming mixed micelles. The primary bile acids, cholic and chenodeoxycholic, are transformed by the enteric bacteria into secondary bile acids, respectively deoxycholic and lithocholic acid. Before this process, the bile acids conjugated with glycine and taurine are also partially deconjugated or hydrolyzed by the enteric bacterial flora. The chenodeoxycholic (CDCA) and ursodeoxycholic (UDCA) acids are widely used in the treatment of the cholesterol binary lithiasis as alternative to surgical operation, as reported by Thistle J. L. e Hofmann A. F. in *New Engl. J. Med.*, 289, 655 (1973) and by Maton P. N. et al. in *Lancet*, 2, 1297 (1977). Other therapeutical applications reported in literature refer to the treatment of the hepatopathies, described by Poupon R. et al. in *Lancet*, 1, 834 (1987), of the gastritis from billiary reflux: described by Stefaniwsky A. B. et al. in *Gastroenterology*, 89, 1000 (1985) and of the cystic fibrosis. The chenodeoxycholic acid (CDCA) has been the first bile acid used in the therapy of the cholesterol billiary calculosis; it is still used notwithstanding its scarce tolerability because its chronic use causes many side effects like diarrhea and raising of the hepatic enzymes (transaminase) that limit its therapeutical use. This compound is very effective in inhibiting the hepatic synthesis of the cholesterol (HMGCoA reductase) so that a bile undersaturated of cholesterol is produced; moreover the high detergence of the CDCA makes easier the disintegration of the gall-stones into the bile in the form of a micellar solution. The CDCA, moderately toxic both at the intestinal and hepatic level, is metabolized into the organism to lithocholic acid, a highly hepatotoxic bile acid. The metabolism of the CDCA in man generally takes place by intestinal absorption through a passive mechanism, conjugation with glycine and taurine from the liver, biliary secretion in these chemical forms which subsequently are absorbed through a passive (glycoconjugate) and active (tauroconjugate and glycoconjugate) mechanism. Throughout this enterohepatic circulation the molecule is partly absorbed and partly eliminated in the feces. The CDCA's epimer known as ursodeoxyoholic acid (UDCA), which differs from the CDCA only because of the orientation of the hydroxyl in position 7 (from 7α to 7β), has been introduced into therapeutic use in 1980 to obviate the side effects of the CDCA. This structural modification, apparently very small, indeed causes deep changes both in the chimico-physical and in the pharmacotoxicological properties. In particular the UDCA is a molecule much more hydrophilic and less detergent than the CDCA and also the other bile acids normally present in the human bile like the deoxycholic and the cholic acid. While the chronic administration of CDCA causes its enrichment in the bile equal to about 90% of the overall bile acids, the administration of the same dosage of UCDA causes an enrichment not greater than 50% of the overall bile acids. This fact can be attributed to various factors like the failure to inhibit the synthesis of the endogenous bile acids from cholesterol and the incomplete intestinal absorption of this latter. More recent studies showed how the mechanism of action responsible for the dissolution of the gall-stones from the UDCA is different from that of the CDCA. The UDCA is able to dissolve the gall-stones by means of a selective reduction of the biliary secretion of cholesterol coupled with an intestinal malabsorption of the cholesterol itself. The UDCA is not so active as the CDCA in inhibiting the synthesis of the cholesterol and of the bile acids from the cholesterol. A bile enriched 50% of UDCA or of its conjugates with glycine and taurine makes a mesophase with the cholesterol and the phospholipids and the mechanism of dissolution of the cholesterol takes place not through micelles but through a system containing also liposomes made by biliary phospholipids. The pharmacokinetic of the UDCA is similar to that of CDCA: the drug is absorbed in the first step through a passive mechanism, transported to the liver from the portal system, conjugated with glycine and taurine and so secreted to be reabsorbed through an active mechanism in glycoconjugate and tauroconjugate form at the ileum level. Also the UDCA is partly 7-dehydroxylated producing lithocholic acid, but with a slower kinetic than that of CDCA. This fact, coupled with the lower absorption at the intestinal level, makes the UDCA a molecule much less toxic than the CDCA, innocuous also at dosages ten times higher than the therapeutic doses. For these reasons the UDCA has been proposed in the last years as new drug in the hepatic pathologies and has proved its effectiveness in the therapy of the primitive biliary cirrhosis and of some kinds of cholestatic hepatopathies. The therapeutic indication of the UDCA is therefore both for the dissolution of the gall-stones of cholesterol and for the treatment of hepatopathies. Lastly it has to be taken into account that the form that accumulates in the organism after chronic administration of UDCA is not the drug itself but its hepatic metabolites, i.e. its conjugate forms, GUDCA and TUDCA, that probably are the active principles. These conjugate forms undergo a process of deconjugation and of 7-dehydroxylation to lithocholic acid from the intestinal bacterial flora and therefore the UDCA in this way loses part of its therapeutic effectiveness and increases its toxicity. To get around these serious drawbacks, new steroid derivatives have been synthesized, having a structure correlated with that of the ursodeoxycholic, hyodeoxycholic and hydroholic acids, in which the acidic function in position 24 is substituted with an amide function stable to the degradation caused by the intestinal bacteria in comparison with the physiological amides containing glycine and taurine. The selection of the amides has been carried out so that the resulting molecules assume the chimico-physical and pharmacological activities necessary to get a good therapeutical effectiveness and a low toxicity. The structural changes introduced affect the chimico-physical properties of the derivatives making easier their absorption and secretion during the permanence in the enterohepatic circulation because the changes of ionization and hydrophobicity affect the transportation of these substances in the hepatobiliar system and in particular reduce the metabolic workload of the liver to conjugate the molecules and contemporaneously significantly reduce the intestinal process of 7-dehydroxylation to lithocholic acid The structural changes favourably affect also the pharmacological properties of these new amides by increasing their effect on the dissolution of the gall-stones from cholesterol and also by means of a choleretic effect in the cholestatic pathologies. Because of these reasons the derivatives of the bile acids object of the present invention can find useful therapeutical application in the treatment of many pathologies of the hepatic tract like the dissolution of the gall-stones from cholesterol, the pathologies coming from cholestasis, in particular the chronic cholestatic hepatitis, the primitive biliary cirrhosis and the juvenile hepatopathy from cystic fibrosis.

DESCRIPTION OF THE INVENTION

One object of the invention is to provide amides between ursodeoxycholic, hyocholic and hyodeoxycholic acids and cyclic aminoacids of general formula

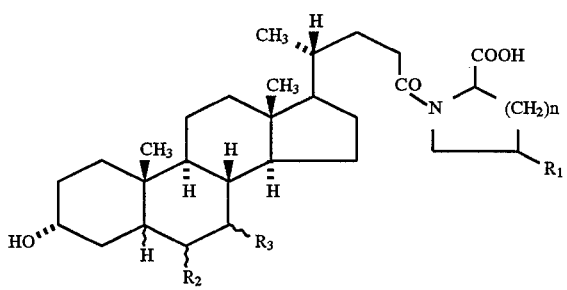

and their pharmacologically acceptable organic or inorganic salts, which can be advantageously used in therapy of the biliary calculosis from cholesterol and of the pathologies caused by cholestasis. In the general formula $R_1$ represents an hydrogen atom or a $(C_1-C_6)$-alkyl, straight or branched, hydroxyl, $(C_1-C_6)$-alkoxyl, straight or branched, sulphydryl or $(C_1-C_6)$-thioalkoxyl, straight or branched, group while n represents an integer number comprised between 1 and 3; $R_2$ represents an hydrogen atom in the case of the ursodeoxycholic acid or an hydroxyl group in position α in the case of the hyocholic and hyodeoxycholic acids. $R_3$ represents an hydrogen atom in the case of the hyodeoxycholic acid, a hydroxyl group in position in the case of the hyocholic acid and in position β in the case of the ursodeoxycholic acid. The compounds preferred according to the invention are those where the aminoacid is proline, 4-(trans)-hydroxyproline, 4-(trans)-thiohydroxyproline, 4-(trans)-methoxyproline or pipecolinic acid, all either as racetalc compounds or as single optical isomers. A further object of the invention is the use of the compounds of general formula I, of their pharmacologically acceptable organic or inorganic salts and of the pharmaceutical compositions containing them in the treatment of the biliary calculosis from cholesterol and and in all the pathologies caused by cholestasis like the chronic cholestatic hepatitis, the primitive biliary cirrhosis and the juvenile hepatopathy connected to cystic fibrosis. The compounds according to the invention are administered preferably by the oral route in conventional pharmaceutical forms selected from tablets, capsules, sugar coated tablets and granulates that can contain, together with the active principle, the several binding, disintegrating, lubrificating, sweetening, flavouring, colouring and coating agents normally used in the pharmaceutical technique. These pharmaceutical forms can be both at immediate release and at controlled or delayed release so that they can be administered one or more times a day and can contain from 100 to 750 mg of the active principle. The therapeutic dosage, dependent both on the body weight and the physical state of the patient and on the gravity of the pathology, is generally comprised between 5 and 15 mg/kg/die. The process of synthesis of the compounds of general formula I takes place by reacting, in an organic solvent selected between straight and cyclic ethers, one molar equivalent of the bile acid with from 1 to 1.2 molar equivalents of an alkyl chloroformate, preferably ethyl or isobutyl chloroformate, in the presence of from 1 to 1.2 molar equivalents of a tertiary organic base, preferably triethylamine or tributylamine at a temperature between 0° C. and 25° C. for a period of time between 15 and 60 minutes. The mixed anhydrides so obtained are reacted, without isolating them, with from 1 to 1.5 molar equivalents of the appropriate aminoacid dissolved in an aqueous alkaline solution containing the amount of base, preferably sodium hydroxide, necessary for the salification of the aminoacid. The temperature is slowly raised to room temperature for a period of time between 2 and 24 hours and then the reaction mixture is added to ice and brought to a pH between 1.5 and 3 by adding a concentrated solution of hydrochloric acid. The crude products are recovered from the reaction mixtures by filtration and can be further purified either by chromatography on silica gel column or by fractional precipitation of the unreacted residue of the starting bile acid and, if necessary, by subsequent crystallization. The amides of the bile acids so obtained can be salified according to methods known in the art with organic or inorganic bases capable to give pharmacologically acceptable salts. Salts of inorganic bases, like sodium and potassium hydroxide, and of organic bases, like trietnylamine and triethanoiamine, are preferred in the present invention. The amides of the bile acids described in the present invention have been analytically characterized by means of spectrophotometric techniques and of elementar analysis. The I.R. spectrum has been obtained by means of a Perkin-Elmer 281/B spectrophotometer generally, when not otherwise specified, by preparing the specimen in nujol and recording the spectrum between 4000 and 600 nm. The $^1$H-NMR spectrum has been recorded at room temperature by means of a 200 MHz Varian Gemini spectrometer, in the reported solvents, by using tetramethylsilane as internal standard. The resonances have been expressed as p.p.m. The $^{13}$C-NMR spectrum has been recorded at 50.3 MHz by means of a Varian Gemini 200 spectrometer by using tetramethylsilane as internal standard and as solvents those described in the experimental section. The chromatographies on silica gel have been carried out by using silica gel 60 F254 (230–400 mesh—E. Merck) and the eluents disclosed in the examples, according to the method described by Clark Still W. et al. in *J. Org. Chem.*, 43, 2923, (1978). Other chimico-physical characteristics of the derivatives object of the present invention have been determined through tests normally used on similar steroidal substances and are recorded in table 1.

In particular the following properties have been checked:
1) Detergence (Critical Micellar Concentration) (CMC)
2) Lipophilia (on HPLC in inverted phase C-18)
3) Solubility of the protonated form
4) Acidity (pKa)
5) CMpH: value of pH at which the acid dissolves in the intestine in a micellar solution.

All the parameters have been determined according to the methods reported by Roda A. et al. in *J. Pharm. Sci.*, 77, 596–605 (1988). The compounds of the present invention show values comparable to those of the analogous physiological compounds as regards the value of detergence defined as cntical micellar concentration (CMC). The compounds of example 3, 5, 7 and 8 have been the least detergent derivatives while the compounds of examples 1, 2 and 6 show a moderate detergent power, similar to that of the analogous physiological compounds conjugated with glycine and taurine. The value of critical micellar concentration held to be ideal to warrant a good hepatic transportation has to be more than 10 mM, i.e. the detergent power has to be relatively low according to considerations of structure-activity relationship (SAR) both on the UDCA and on a series of physiological bile acids. All the derivatives synthesized, except those described in examples 4 and 6, show a CMC value higher than 10, however it has to be taken into account that the conjugate with taurine, TUDCA, shows a value of 8, likewise the compounds described in examples 4 and 6. The values of lipophilia, dependent on the substituents introduced, are comprised between that of UDCA, considered equal to 1, and those of the physiological conjugates TUDCA and GUDCA. The optimum value of lipophelia for the bile acids is held to be rK'≧0.6, the optimum choice has to be considered a high lipophilia joined to a low detergence. The molecule having such characteristics is not much toxic and at the same time, if enough lipophilic, it can split up into the membrane and so warrents an effective absorption also with a mechanism of passive diffusion. All the derivatives synthesized show a favourable combination of such characteristics. All the compounds of the present invention show a value much higher than that of the analogous natural compounds as regards the value of solubility of the protonated form and the values of the compounds of examples 1 and 2 are particularly meaningful. The solubility of the protonated form in micellar solution, expressed by the CMpH value, is analogous to that of the natural conjugate with glycine and lower than that of the ursodeoxycholic acid for all the compounds synthesized. The values of pKa are optimal to warrant the ionization of the compounds of the invention at the pH of the intestine and therefore make easier the formation of the soluble ionized salt and the formation of micelles being the ideal value between 3.5 and 4.5 likewise to what occurs for the GUDCA. The value of the pKa together with that of the CMC accounts for the possibility of the compounds of the invention of dissolving themselves at a pH between 4 and 7 so permitting to the molecules of reaching the intestine after protonation at the stomach level. All the synthesized substances show a profile of such chimico-physical characteristics favourable in comparison with those of the physiological bile acids and of their conjugates.

TABLE 1

Chimico-physical properties

| Bile acids | Detergence (CMC) (mM) | Lipophilia rk'* | Solubility (µM) | CMpH | pKa |
|---|---|---|---|---|---|
| UDCA | 19 | 1 | 9 | 8.44 | 5 |
| GUDCA | 12 | 0.67 | 3 | 5.05 | 3.9 |
| TUDCA | 8 | 0.63 | n.d. | n.d. | 1 |
| Example 1 | 15 | 0.81–1 | 113 | 6.01 | 3.9 |
| Example 2 | 10 | 0.52 | 250 | 4.62 | 3.8 |
| Example 3 | 29 | 0.71 | 30 | 6.16 | 3.4 |
| Example 4 | 6.5 | 0.85 | 59 | 5.08 | 3.8 |
| Example 5 | 25 | 0.83–1 | 32 | 6.30 | 3.5 |
| Example 6 | 8 | 1–1.04 | 20 | 7.2 | 3.9 |
| Example 7 | 30 | 0.85 | 60 | 6.2 | 3.8 |
| Example 8 | 25 | 0.94 | 52 | 5.8 | 3.9 |

* = referred to the K' of the ursodeoxycholic acid
n.d. = not determined

The biliary pharmacokinetic of the amides object of the present invention after their administration in the rat by intravenous route at the dosage of 10 µmoles/min/kg has been evaluated according to the method reported by Roda A. et al. in *J. Pharm. Sci.* 77, 596–605, (1988) and expressed with the following parameters: bile volume, bile acids secretion (Table 2), phospholipids secretion, cholesterol secretion (Table 3). The values of the volume of the maximum biliary secretion ($SM_B$) and of the biliary secretion remaining at the end of the test ($SR_B$) are expressed as ml/min/kg The values of secretion of the bile acids, maximum ($SM_{AB}$) and remaining ($SR_{AB}$), of the phospholipids, maximum ($SM_{PL}$) and remaining ($SR_{PL}$) and of the cholesterol, maximum ($SM_C$) and remaining ($SR_C$) are expressed as µmoles/min/kg. The times necessary to reach the maximum values of reaction (Tmax) are expressed as minutes.

TABLE 2

Pharmacokinetic data

| Bile acids | BILE VOLUME (ml/min/kg) | | | BILE ACIDS SECRETION (µmoles/min/kg) | | |
|---|---|---|---|---|---|---|
| | $SM_B$ | $SR_B$ | Tmax (min) | $SM_{AB}$ | $SR_{AB}$ | Tmax (min) |
| UDCA | 0.12 ± 0.05 | 0.05 ± 0.01 | 60 | 4.2 ± 1.2 | 1.5 ± 0.7 | 30 |
| GUDCA | 0.08 ± 0.01 | 0.04 ± 0.01 | 45 | 6.1 ± 3.3 | 0.8 ± 0.1 | 45 |
| TUDCA | 0.07 ± 0.01 | 0.05 ± 0.01 | 60 | 7.5 ± 1.8 | 0.4 ± 0.1 | 30 |
| Example 1 | 0.09 ± 0.02 | 0.05 ± 0.01 | 60 | 6.0 ± 1.8 | 0.9 ± 0.2 | 60 |
| Example 2 | 0.10 ± 0.01 | 0.04 ± 0.005 | 60 | 6.3 ± 1.0 | 0.9 ± 0.2 | 60 |
| Example 3 | 0.09 ± 0.02 | 0.03 ± 0.005 | 45 | 11.1 ± 2.1 | 0.8 ± 0.6 | 60 |
| Example 4 | 0.07 ± 0.01 | 0.05 ± 0.002 | 60 | 7.9 ± 0.8 | 1.6 ± 0.1 | 60 |
| Example 5 | 0.09 ± 0.02 | 0.04 ± 0.01 | 60 | 7.3 ± 3.2 | 1.0 ± 0.4 | 60 |
| Example 6 | 0.12 ± 0.02 | 0.06 ± 0.02 | 60 | 7.2 ± 1.5 | 0.8 ± 0.08 | 60 |
| Example 7 | 0.06 ± 0.01 | 0.04 ± 0.003 | 60 | 6.0 ± 0.2 | 1.8 ± 0.05 | 60 |
| Example 8 | 0.07 ± 0.01 | 0.05 ± 0.005 | 60 | 5.7 ± 0.5 | 1.4 ± 0.02 | 60 |

TABLE 3

Pharmacokinetic data

| Bile acids | PHOSPHOLIPIDS SECRETION (μmoles/min/kg) | | | CHOLESTEROL SECRETION (μmoles/min/kg) | | |
|---|---|---|---|---|---|---|
| | $SM_{PL}$ | $SR_{PL}$ | Tmax (min) | $SM_C$ | $SR_C$ | Tmax (min) |
| UDCA | 0.26 ± 0.13 | 0.12 ± 0.03 | 45 | 0.07 ± 0.04 | 0.03 ± 0.02 | 60 |
| GUDCA | 0.23 ± 0.08 | 0.10 ± 0.01 | 45 | 0.06 ± 0.02 | 0.03 ± 0.01 | 30 |
| TUDCA | 0.20 ± 0.01 | 0.07 ± 0.02 | 45 | 0.04 ± 0.01 | 0.02 ± 0.01 | 45 |
| Example 1 | 0.28 ± 0.07 | 0.11 ± 0.01 | 45 | 0.06 ± 0.02 | 0.04 ± 0.01 | 45 |
| Example 2 | 0.25 ± 0.05 | 0.12 ± 0.01 | 60 | 0.08 ± 0.03 | 0.04 ± 0.01 | 30 |
| Example 3 | 0.28 ± 0.03 | 0.12 ± 0.01 | 45 | 0.03 ± 0.003 | 0.02 ± 0.006 | 30 |
| Example 4 | 0.15 ± 0.06 | 0.09 ± 0.02 | 60 | 0.06 ± 0.01 | 0.04 ± 0.01 | 60 |
| Example 5 | 0.30 ± 0.04 | 0.12 ± 0.04 | 60 | 0.08 ± 0.04 | 0.04 ± 0.02 | 60 |
| Example 6 | 0.37 ± 0.08 | 0.12 ± 0.03 | 60 | 0.06 ± 0.01 | 0.03 ± 0.007 | 60 |
| Example 7 | 0.28 ± 0.04 | 0.26 ± 0.02 | 90 | 0.06 ± 0.05 | 0.03 ± 0.01 | 30 |
| Example 8 | 0.34 ± 0.07 | 0.21 ± 0.04 | 60 | 0.09 ± 0.03 | 0.06 ± 0.002 | 30 |

The compounds claimed in the present invention show a choleretic effect comprised between the effect caused by TUDCA and GUDCA (0.07 ml/min/kg) and that caused by UDCA (0.12 ml/min/kg). The compounds of formula I are secreted in the bile without undergoing substantial hepatic metabolism differently from the UDCA that has to be conjugated with glycine and/or taurine in order to be secreted. The maximum biliary secretion, obtained with the compound of example 3, is remarkably greater than that obtained with the conjugate bile acids, while all the other compounds show a value similar to that of TUDCA and GUDCA. The value of secretion of the bile acids partly expresses the effect of the administration of the compound on the transport with albumin to the liver and therefore on the hepatic captation. Moreover a high value of maximum secretion in the bile shows that the molecule possesses proper chimico-physical properties and that it has not to be transformed by the liver to more polar metabolites to be secreted. All the compounds exemplified show values of biliary secretion of phospholipids similar to those of the natural products except for the compounds 6 and 8 where the values of $SM_{PL}$ are significantly increased. The maximum secretion of the cholesterol is similar to the controls except for compound 3 where it is significantly reduced.

BRIEF DESCRIPTION OF THE DRAWING

The invention is further illustrated in FIG. 1 which shows the kinetic of absorption on an ileal loop of the isolated and perfused intestine of rabbit, expressed in micromoles of a compound of Formula I, per minute per centimeter, compared with the two physiological conjugate bile acids, GUDCA and TUDCA, according to the method of R. Aldini Eur. Surg. Res. 22, 93–100 (1990).

All the compounds studied show a kinetic of absorption of active type similar to that of TUDCA and GUDCA. The type of kinetic observed is in accordance with the structure of the compounds characterized by the presence of the amidic bond, hence in conjugate form, fundamental for the receptorial recognition of the system active carrier. The intestinal and hepatic metabolism of the amides object of the present invention has been studied to determine their stability and hence the possibility of accumulation in the enterohepatic circulation. The stability taken into account is that related to the pancreatic enzymes like the carboxypeptidases that breaks the amidic bond created during the process of conjugation and to the bacteria of the intestinal flora which, together with the enzyme cholylglycine hydrolase, are responsible for deconjugation and 7-dehydroxylation. In the enterohepatic circulation there is a continuous intestinal deconjugation and hepatic reconjugation of the bile acid and therefore the biological half-like of the conjugate molecule is relatively short. The rationale of the search of new bile acids metabolically stable at hepatic and intestinal level lies in the fact that conjugate products more hydrophilic and soluble at lower values of pH persist longer time in the enterohepatic circulation. As a matter of fact, for instance, the conjugation makes the UDCA more hydrophilic and soluble at lower values of pH having a pKa equal to 3.9 for the GUDCA and equal to about 1 for the TUDCA. The parameters related to the intestinal metabolism have been determined according to the method described by Roda A. et al. in J. Lipid Res., 31, 289–298, (1990) and are reported in table 4. The compounds of formula I treated with cholylglycine hydrolase, enzyme able to hydrolyze the amidic bond of TUDCA and GUDCA in position C-24, show a high stability and only for the compound of example 6 a moderate hydrolysis, definitely lower than the degree of hydrolysis of the physiologial conjugates TUDCA and GUDCA, has been documented. The decidedly higher stability of the compounds of formula I in comparison with the physiological conjugates TUDCA and GUDCA is held to be due to the fact that the nitrogen atom of the amidic bond of the compounds of formula I is a member of a cyclic ring and that therefore there are factors of steric hindrance that prevent the attack of the enzyme cholylglycine hyrolase. The stability of the molecules has been evaluated in vitro in the presence of intestinal bacteria, in such conditions that it is possible to evaluate both the process of deconjugation and that of 7-dehydroxylation. All the compounds studied show a high stability when incubated under anaerobic conditions with human feces, while the analogous GUDCA and TUDCA are quickly metabolized to lithocholic acid.

TABLE 4

Figure 1:
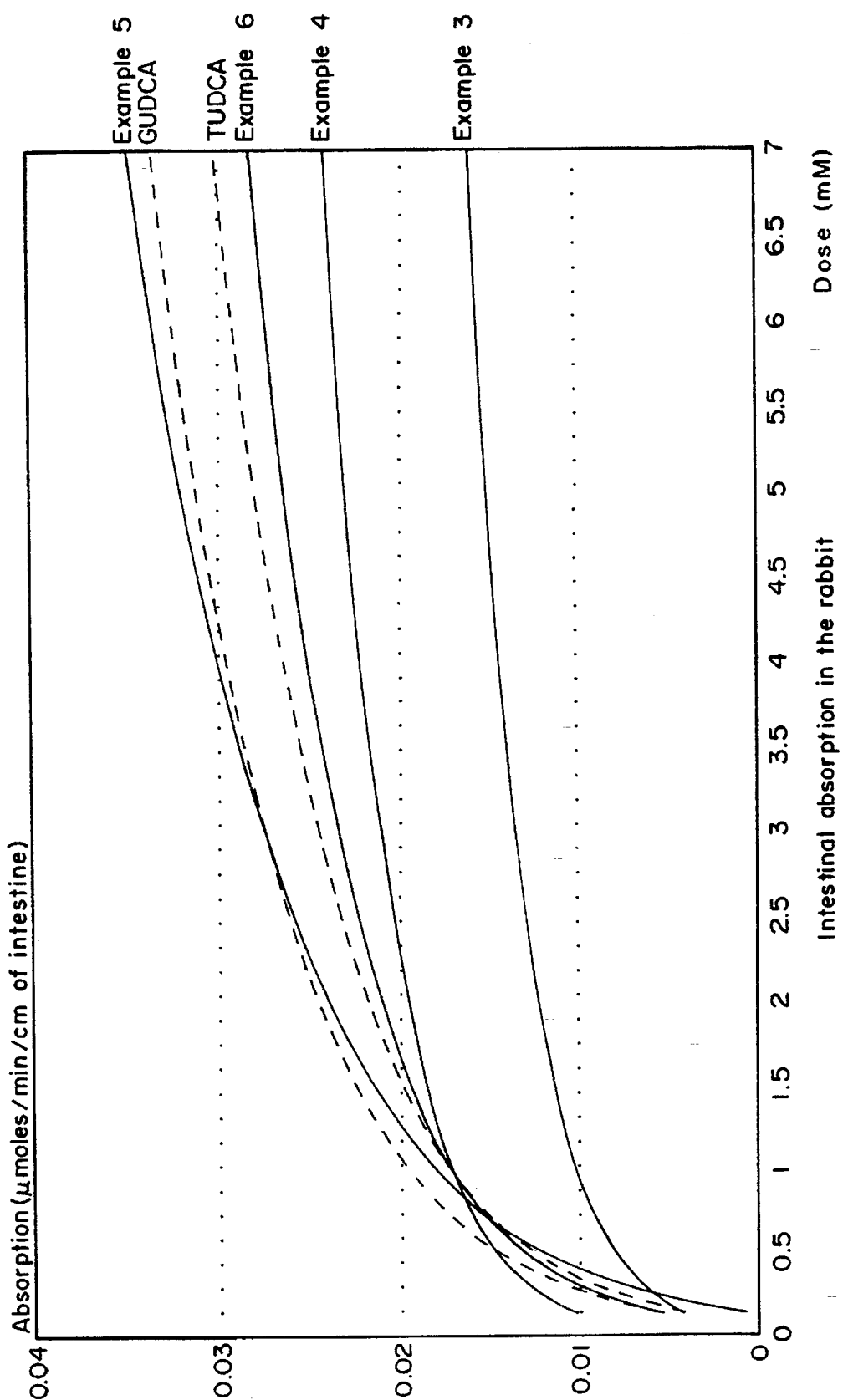

| | Evaluation of the metabolic stability | |
|---|---|---|
| Bile acids | Stability to the cholylglycine hydrolase t/2 (hours) | Stability to anaerobic intestinal bacteria t/2 (hours) |
| UDCA | <0.5 | 2 |
| GUDCA | 4 | 2 |

TABLE 4-continued

Evaluation of the metabolic stability

| Bile acids | Stability to the cholylglycine hydrolase t/2 (hours) | Stability to anaerobic intestinal bacteria t/2 (hours) |
|---|---|---|
| TUDCA | 4 | 2 |
| Example 1 | >72 | >72 |
| Example 2 | >72 | >72 |
| Example 3 | >72 | >72 |
| Example 4 | >72 | >72 |
| Example 5 | >72 | >72 |
| Example 6 | 24 | 12 |
| Example 7 | >72 | >72 |
| Example 8 | >72 | >72 | t/2 = biological half-life of the molecules (expressed as hours).

The hepatic metabolism has been evaluated by means of intravenous infusion of the products followed by HPLC determination of the chemical forms recovered in the secreted bile. All the compounds of formula I have efficiently been picked up by the liver and rapidly secreted into the bile without undergoing any biotransformation, contrary to the UDCA which has conjugated itself with glycine and taurine to be secreted. The data obtained show the good preservation of the compounds of formula I as such in the enterohepatic circulation, with an increased biological half-life and without formation of toxic or in any case unwanted metabolites. The pharmacology of the amides object of the present invention has mainly been studied by evaluating the ability to prevent a hepatic damage caused by a very detergent and toxic bile acid like the taurochenodeoxycholic acid (TCDCA) by means of the compounds object of the present invention, according to the method described by Schmucker D. L. et al. in Hepatology, 12, 1216–1221, (1990) The parameters evaluated in table 5 are the hepatic damage expressed as number of necrotic cells, the calcium content in the bile expressed as μmoles/min/kg, the biliary content of lactatodehydrogenase (LDH) and of alkaline phosphatase (ALP) expressed as IU/L. The increase of the excretion of the enzymes LDH and ALP and the diminution of the calcium content represent a sign of the hepatotoxicity caused by the TCDCA. All the compounds of formula I have been able to prevent the hepatic damage caused by the toxic compound when they have been infused by the intravenous route together with the toxic compound at an equimolecular dose (8 μmoles/min/kg). All the compounds according to the invention, with the partial exception of those of examples 6 and 8, have proven to be more powerful than the natural compounds as shown by the histochemical evaluation of the cellular damage and by the lowered biliary release of LDH and ALP.

TABLE 5

Evaluation of the cytochemical and biochemical parameters related to the protection of the hepatocellular damage caused by the infusion of taurochenodeoxycholic acid (TCDCA) in the rat

| Bile acids | Cellular damage | Ca Output (μmol/min/kg) | LDL (IU/L) | ALP (IU/L) |
|---|---|---|---|---|
| UDCA | 5 ÷ >20 | 0.15 ÷ 0.22 | 60 ÷ 171 | 214 ÷ 221 |
| GUDCA | 5 ÷ 10 | 0.16 ÷ 0.26 | 30 ÷ 44 | 93 ÷ 129 |
| TUDCA | 0 ÷ 1 | 0.23 ÷ 0.37 | 34 ÷ 38 | 63 ÷ 116 |
| Example 1 | 0 ÷ 3 | 0.3 ÷ 0.52 | 14 ÷ 15 | 30 ÷ 31 |
| Example 2 | 5 ÷ 6 | 0.32 ÷ 0.42 | 1 ÷ 18 | 17 ÷ 45 |
| Example 3 | 2 ÷ 3 | 0.64 ÷ 0.79 | 7 ÷ 21 | 22 ÷ 39 |
| Example 4 | 1 ÷ 2 | 0.32 ÷ 0.45 | 63 ÷ 80 | 26 ÷ 34 |
| Example 5 | 3 ÷ 4 | 0.30 ÷ 0.37 | 10 ÷ 12 | 53 ÷ 78 |
| Example 6 | 0 ÷ 1 | 0.42 ÷ 0.46 | 99 ÷ 227 | 42 ÷ 122 |
| Example 7 | 3 ÷ 4 | 0.39 ÷ 0.40 | 46 ÷ 51 | 27 ÷ 42 |
| Example 8 | 1 ÷ 7 | 0.40 ÷ 0.44 | 66 ÷ 125 | 48 ÷ 67 |

The compound of example 1 has been evaluated as regards its effectiveness in lowering the histological and biochemical alterations caused by cholestasis following the ligature of the bile duct, as reported by Poo J. L. in Gastroenterology, 102, 1752– 1759, (1992). Parameters of histological type like the weight of the liver and the cholangiofibrosis expressed both as deposit of collagenous fibres and as proliferation of the bile ducts, and of biochemical type like the concentration of the alkaline phosphatase (ALP) and of the lactatodehydrogenase (LDH) have been evaluated in the following table 6. The weight of the liver is expressed as grams/100 grams of body weight, the deposit of collagenous fibres is expressed as area in pixel, while the proliferation of the bile ducts is expressed through the coloration of the sections and the evaluation of the enzyme yGT by indirect lecture of the optical density (O.D.) while the alkaline phosphatase and the lactatodehydrogenase are expressed as IU/L.

TABLE 6

Evaluation of the histological and biochemical parameters related to the protection of the damage caused by the ligature of the bile duct in the rat.

| Compound | liver's weight (g/100 g body weight) | areas (pixels) | Optical Density | ALP (IU/L) | LDH (IU/L) |
|---|---|---|---|---|---|
| UDCA | 6.2 ± 0.4 | 0.50 ± 0.05 | 87.83 ± 14.24 | 5.50 ± 0.90 | 509 ± 39.4 |
| TUDCA | 5.1 ± 0.3 | 0.47 ± 0.05 | 82.89 ± 12.72 | 3.50 ± 1.06 | 487 ± 36.5 |
| Example 1 | 6.3 ± 0.6 | 0.39 ± 0.04 | 73.07 ± 11.79 | 8.30 ± 1.55 | 395 ± 32.8 |
| Physiological Solution | 6.9 ± 0.9 | 0.42 ± 0.04 | 56.34 ± 16.27 | 49.00 ± 6.72 | 452 ± 51.2 |

The examined compound has shown a decrease of the liver's weight in comparison with that of the control animals treated with physiological solution, with a value similar to that of the UDCA. The results of the videocytometric measures show a moderate decrease in the deposit of collagenous fibres and in the proliferation of the bile ducts for the compound of example 1 in comparison both with UDCA and TUDCA. The treatments with UDCA, TUDCA and compound of example 1 have drastically reduced the plasmatic concentration of ALP showing for all the compounds a similar capability to limit the seriousness of the hepatic damage. Lastly, only the compound of example 1 has been able to lower the plasmatic levels of LDH in comparison with the untreated group and with those treated with natural bile acids. The chimico-physical and biological data, reported in the present invention, show a significant pharmacological improvement of the compounds of the examples in comparison with the analogous natural compounds. The structural modifications introduced make the molecules more hydrophilic than the UIDCA and with a similar detergence, such properties are able to make the bile more hydrophilic and less detergent in comparison with that containing natural bile acids with the end result of a lower toxicity of membrane. Moreover the structural modifications introduced have remarkably improved the metabolic stability by producing a double positive effect as all the compounds are not deconjugated in the lateral chain and, consequently, are not 7-dehydroxylated in the steroidal ring. Such effect is of great importance both to increase the biological half-life of these compounds and to lower the formation of potentially toxic metabolites like the lithocholic acid. All the derivatives show a remarkable effect on the biliary lipidic secretion by keeping a proper secretion of phospholipids and cholesterol. In particular, the compound of example 3 is able to selectively lower the secretion of the cholesterol with the end result of a production of bile undersaturated in cholesterol and strongly enriched in phospholipids and bile acids; in such conditions the bile possesses a potential increased activity in the dissolution of the gall-stones of cholesterol. Moreover the structural modifications have not endangered the transportation both intestinal and hepatic because the compounds according to the invention are absorbed with active and passive mechanism with kinetic parameters similar to those of the natural compounds. Lastly many compounds proved to be able of preventing the hepatic damage caused by TCDCA because of a proper hydrophobic-hydrophilic balance of the molecule coupled with an efficient absorption and transportation of the molecule into the enterohepatic circulation. In conclusion the compounds described have proved to be more active than the natural analogous compounds both in the inhibition of the secretion of the cholesterol, and therefore able to dissolve the gall-stones, and in the treatment of the chronic cholestatic hepatopathies. The examples hereinbelow reported have to be considered as an illustration of the present invention and not as an its limitation.

EXAMPLE 1

N-[(3α,5β,7β)-3,7-Dihydroxy-24-oxocholan-24-yl]-L-proline 19.6 Grams (50 mmoles) of ursodeoxycholic acid (3α, 7β-dihydroxy-5β-cholan-24-oic acid) are suspended in 300 ml of anhydrous dioxane under an atmosphere of inert gas.

The suspension is added to 13.2 ml (55 mmoles) of tributylamine and the temperature is brought to 10° C., then it is slowly added to 5.3 ml (55 mmoles) of ethylchloroformate dissolved in 10 ml of dioxane. After 30 minutes at a temperature of 10° C., a solution containing 6.9 g (60 mmoles) of L-proline dissolved in 25 ml of a 10% (W/V) aqueous solution of sodium hydroxide is dripped into the reaction mixture. The reaction mixture is kept 4 hours under stirring by raising the temperature till room temperature; the reaction mixture is then added to 400 g of ice and acidified to pH 2 with a concentrated solution of hydrochloric acid. A white precipitate forms which is kept 30 minutes under stirring and then filtered and dried under vacuum. The crude product (23.6 g) is purified by fractionated precipitation of the residue of the starting ursodeoxycholic acid; after having dissolved the crude material coming from the reaction in 20 ml of a 2.5N aqueous solution of sodium hydroxide, and a 1N aqueous solution of hydrochloric acid is slowly added until pH 5.4. The suspension is left standing 5 minutes and then the solid is filtered off while the filtrate is brought to pH 1.5 by means of an aqueous concentrated solution of hydrochloric acid while keeping constant the temperature. The purity of the white solid which precipitates (20.7 g) is checked by T.L.C. with tetrahydrofuran as eluent and cerium phosphomolibdate and ammonium nitrate as revealers; in case the chromatography still shows the presence of the UDCA the fractionate precipitation is repeated under the same conditions. The pure product so obtained shows the following chimico-physical characteristics:

I.R. (nujol) cm$^{-1}$: 3360, 1719, 1625

$^1$H-NMR (CDCl$_3$) ppm: 5.0 (broad 2H); 4.57 (t, 1H); 3.6 (m, 4H); 3.0 (m, 2H); 2.4–0.8 (complex system 28H); 1.0 (d, 3H); 0.94 (s, 3H); 0.67 (s, 3H)

$^{13}$C-NMR (CDCl$_3$) ppm: 176.3; 175.0; 72.4; 72.2; 59.3: 57.4; 56.8; 49.5; 49.3; 48.7; 48.4; 45.0; 44.7; 44.3; 41.8; 41.8; 41.0; 38.9; 36.3; 35.4; 31.3; 29.9; 28.2; 24.2; 22.6; 19.4; 12.9

Elementary analysis: calculated C 71.12 H 9.68 N 2.86 found C 72.05 H 9.72 N 2.77

EXAMPLE 2

N-[(3α,5β,7β)-3,7-Dihydroxy-24-oxocholan-24-yl]-4-(trans)-hydroxy-L-proline

The crude product is obtained by means of the same procedure and in the same conditions described in the previous test (example 1) by using 7.86 g (60 mmoles) of (trans)-4-hydroxy-L-proline instead of the L-proline. The crude product (25 g) has been purified by chromatography on silica gel column by using distilled tetrahydrofuran and glacial acetic acid in 98:2 (v/v) ratio as eluent so obtaining 22.8 g of pure product having the following chimico-physical characteristics:

I.R (nujol) cm.$^{-1}$: 3380, 1719, 1625

$^1$H-NMR (CDCl$_3$) ppm: 5.0 (broad 2H); 4.57 (dd, 1H); 3.6 (m, 4H); 3.0 (m, 2H); 2.4–0.8 (complex system 28H); 1.0 (d, 3H); 0.94 (s, 3H); 0.67 (s, 3H)

$^{13}$C-NMR (CDCl$_3$) ppm: 176.3; 174.5; 72.5; 72.3; 60.5; 57.9; 56.9; 49.9; 49.3; 48.8; 48.5; 44.9; 44.4; 41.9; 41.1; 39.0; 36.4; 35.5; 32.7; 31.4; 30.8; 30.1; 26.1; 22.8; 19.0; 13.0

Elementary analysis: calculated C 68.88 H 9.37 N 2.77 found C 69.02 H 9.42 N 2.67

EXAMPLE 3

N-[(3α,5β,7β)3,7-Dihydroxy-24-oxocholan-24-yl]-4-(trans)-methoxy-L-proline

The crude product is obtained by means of the same procedure and in the same conditions described in the test of example 1 by using 8.6 g (60 mmoles) of (trans)-4-methoxy-L-proline instead of the L-proline. The crude product (20.2 g) has been twice purified by chromatography on silica gel column by using as eluent first distilled tetrahydrofuran and then the mixture between distilled tetrahydrofuran and glacial acetic acid in 98:2 (v/v) ratio so obtaining, after crystallization from ethyl ether, 11.6 g of pure product having the following chimico-physical characteristics:

I.R. (nujol) cm$^{-1}$: 3360, 1719, 1625

$^1$H-NMR (CDCl$_3$) ppm: 4.47 (t, 1H); 4.0 (broad 2H): 3.68 (m, 1H); 3.5 (m, 2H); 33 (s, 3H): 2.4–0.8 (complex system 30H); 0.9 (d, 3H); 0.85 (s, 3H); 0.67 (s, 3H)

$^{13}$C-NMR (CDCl$_3$) ppm: 176.3; 174.5; 78.6; 70.9; 65.7; 57.6; 56.6; 54.8; 49.6; 49.3; 48.7; 48.5; 43.5; 43.3; 42.3; 40.0; 39.0; 36.8; 35.3; 33.9; 31.4; 30.5; 29.8; 26.7; 23.2; 21.0; 18.4; 14.9; 12.0

Elementary analysis: calculated C 69.32 H 9.51 N 2.70 found C 69.42 H 9.42 N 2.67

EXAMPLE 4

N-[(3α,5β,7β)-3,7-Dihydroxy-24-oxocholan-24-yl]-D-proline

The crude product is obtained by means of the same procedure and in the same conditions described in the test of example 1 by using 6.9 g (60 mmoles) of D-proline instead of the L-proline. The crude product (21.2 g) has been twice purified by chromatography on silica gel column by using as eluent first distilled tetrahydrofuran and then the mixture between distilled tetrahydrofuran and glacial acetic acid in 98:2 (v/v) ratio so obtaining, after crystallization from ethyl ether, 5.0 g of pure product having the following chimico-physical characteristics:

I.R. (nujol) cm$^{-1}$: 3360, 1719, 1625

$^1$H-NMR (CDCl$_3$) ppm: 4.4 (broad, 2H); 4.35 (t, 1H); 3.6 (m, 4H); 3.0 (m, 2H); 2.4–0.8 (complex system 28H); 1.0 (d, 3H); 0.94 (s, 3H); 0.67 (s, 3H)

$^{13}$C-NMR (CDCl$_3$) ppm: 175.1; 174.0; 72.0; 71.8; 60.3; 57.5: 56.5; 49.8; 48.1; 44.7; 44.4; 44.0; 42.4: 40.6; 36.1; 35.2; 31.9: 29.6; 27.9; 23.9; 22.4; 19.1, 12.7

Elementary analysis: calculated C 71.12 H 9.68 N 2.86 found C 71.92 H 9.70 N 2.90

EXAMPLE 5

N-[(3α,5β,7β)-3,7-Dihydroxy-24-oxocholan-24-yl]-D,L-proline

The crude product as obtained by means of the same procedure and in the same conditions described in the test of example 1 by using 6.9 g (60 mmoles) of D,L-proline instead of the L-proline. The crude product (20.1 g) has been twice purified by chromatography on silica gel column by using as eluent first distilled tetrahydrofuran and then the mixture between distilled tetrahydrofuran and glacial acetic acid in 98:2 (v/v) ratio so obtaining, after crystallization from ethyl ether, 12.8 g of pure product having the following physical characteristics:

I.R. (nujol) cm$^{-1}$: 3360, 1719, 1625

$^{13}$C-NMR (CDCl$_3$) ppm: 176.3; 174.5; 70.9; 67.9; 65.9; 59.1; 55.7; 54.9; 49.5; 49.3; 48.7; 43.8; 43.4; 42.4; 40.1; 36.1; 35.9; 34.8; 31.4; 30.5; 29.8; 29.5; 28.7; 26.6; 24.2; 21.2; 18.5; 15.0; 12.0

Elementary analysis: calculated C 71.12 H 9.68 N 2.86 found C 71.02 H 9.62 N 2.87

EXAMPLE 6

2-Carboxy-N-[(3α,5β,6α,7α)-3,6,7-Trihydroxy-24-oxocholan-24-yl]-L-proline

The crude product is obtained by means of the same procedure and in the same conditions described in the test of example 1 by using 7.75 g (60 mmoles) of D,L-pipecolinic acid instead of the L-proline. The crude product (19.5 g) has been twice purified by chromatography on silica gel column by using as eluent ethyl acetate/methanol/acetic acid in 88:10:2 (v/v) ratio so obtaining 10.8 g of pure product having the following chimico-physical characteristics:

I.R. (nujol) cm$^{-1}$: 3360, 1720, 1610

$^1$H-NMR (CD$_3$OD) ppm: 35 (m, 3H); 2.4 (m, 2H); 2.2–0.8 (complex system 30H); 1.0 (d, 3H); 0.98 (s, 3H); 0.60 (s, 3H)

$^{13}$C-NMR (CDCl$_3$) ppm: 176.0; 175.9; 72.0; 71.8; 62.0; 57.4; 56.4; 49.8; 49.3; 48.9; 44.7; 43.9; 40.6; 38.5; 38.0. 36.8; 36.0 35.0; 27.9; 27.8; 24.0; 23.9, 22.3; 21.1; 19.1; 12.7

Elementary analysis: calculated C 71.52 H 9.81 N 2.78 found C 72.03 H 9.99 N 2.55

EXAMPLE 7

N-[(3α,5α,7α)-3,6,7-Trihydroxy-24-oxocholan-24-yl]-L-proline

The crude product is obtained by means of the same procedure and in the same conditions described in the test of example 1 by using 20.4 g (50 mmoles) of hyocholic acid instead of ursodeoxycholic acid. The crude product (15.0 g) has been purified by flash chromatography on silica gel column by using as eluent ethyl acetate/methanol/acetic acid in 8 5.1:0.5 (v/v) ratio so obtaining 8 g of pure product having the following chimico-physical characteristics:

I.R. (nujol) cm$^{-1}$: 3360, 1715, 1630

$^1$H-NMR (CDCl$_3$) ppm: 5.1 (broad, 1H); 4.6 (t, 1H); 3.72 (m, 6H); 3.0 (m, 2H); 2.5–0.9 (complex system 27H); 1.03 (d, 3H); 0.95 (s, 3H); 0.69 (s, 3H)

$^{13}$C-NMR(CDCl$_3$) ppm: 176.3; 175.5; 70.9; 67.9; 64.9; 59.1; 56.8; 54.9; 49.5; 49.3; 48.7; 43.8; 43.4; 42.4; 40.1; 39.1; 35.9; 34.8; 31.4; 30.5; 29.8; 28.9; 28.7; 26.6; 24.2; 21.2; 18.5; 15.0; 12.3

Elementary analysis: calculated C 68.86 H 9.37 N 2.77 found C 68.70 H 9.42 N 3.00

EXAMPLE 8

N-[(3α,5β,6α)-3,6-Dihydroxy-24-oxocholan-24-yl]-L-proline

The crude product is obtained by means of the same procedure and in the same conditions described in the test of example 1 by using 19.6 g (50 mmoles) of hyodeoxycholic acid instead of ursodeoxycholic acid. The crude product (24.9 g) has been purified by flash chromatography on silica gel column by using as eluent ethyl acetate/methanol/acetic acid in 8.5:1:0.5 (v/v) ratio so obtaining 13 g of pure product having the following chimico-physical characteristics:

I.R. (nujol) cm$^{-1}$: 3360. 1719. 1625

$^1$H-NMR (CDCl$_3$) ppm: 410 (broad: 2H); 3.8 (m, 2H); 3.5 (m, 2H); 3.3 (t, 1H); 2.4–0.8 (complex system 29H); 0.9 (d, 3H); 0.85 (s, 3H); 0.60 (s, 3H)

$^{13}$C-NMR (CDCl$_3$) ppm: 176.4; 174.5; 70.8; 67.7; 65.9; 59.2; 55.7; 54.8; 49.4; 49.3; 48.6; 43.9; 43.2; 42.1: 40.1; 36.1; 35.9; 34.7; 31.2; 30.4; 29.8; 29.5; 28.6; 26.5; 24.0; 21.0; 18.4; 14.8; 11.9

Elementary analysis calculated C 71.12 H 9.68 N 2.86 found C 70.97 H 9.62 N 2.87

EXAMPLE 9

N-[(3α,5β,7β)-3,7-Dihydroxy-24-oxocholan-24-yl]-4-(cis)-thiohydroxy-L-proline 1.96 Grams (5 mmoles) of ursodeoxycholic acid are suspended in 30 ml of anhydrous dioxane, under an atmosphere of inert gas, this suspension is added to 1.32 ml (5.5 mmoles) of tributylamine and, after having brought to 10° C. the temperature of the reaction mixture, 0.53 ml (5.5 mmoles) of ethylchloroformate are dripped. The temperature of the reaction is kept at 10° C. for 1 hour; then 0.69 g (6 mmoles) of 4-(cis)-thiohydroxy-L-proline dissolved in 2.5 ml of a 10% (w/v) aqueous solution of sodium hydroxide are added and the reaction mixture is kept at room temperature overnight. After having dried the reaction mixture, a 1N aqueous solution of hydrochloric acid is added, at the temperature of 0° C., until pH 1 and the precipitate is homogenized, recovered by filtration and dried under vacuum with a yield equal to 82%. The pure product so obtained shows the following chimico-physical characteristics:

I.R. (nujol) cm$^{-1}$: 3400, 1719, 1680

$^{1}$H-NMR (CD$_3$OD) ppm: 4.05 (m, 1H); 3.5 (m, 2H); 3.35 (m, 1H); 2.8–1.0 (complex system 30H); 1.0 (d, 3H); 0.95 (s, 3H); 0.60 (s, 3H)

Elementary analysis: calculated C 66.76 H 9.08 N 2.69 S 6.14 found C 66.20 H 9.40 N 2.79 S 6.01

We claim:

1. An amide of formula I

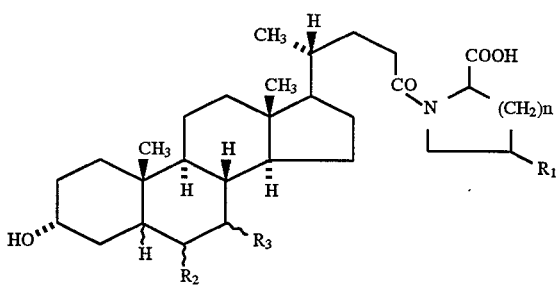

wherein $R^1$ is a hydrogen atom, a hydroxyl group, a sulphydryl group, a straight or branched $C_{1-6}$alkyl group, a straight or branched $C_{1-6}$alkoxyl group, or a $C_{1-6}$thioalkoxyl group; n is an integer from 1 to 3; $R^2$ is a hydrogen atom or a hydroxyl group; or $R^3$ is a hydrogen atom or a hydroxyl group, and a pharmacologically acceptable organic or inorganic salt thereof.

2. The amide according to claim 1 wherein said organic salt is triethylamine or the triethanolamine salt and said inorganic salt is the sodium or potassium salt.

3. An optical isomer or racemate of the amide according to claim 1 wherein n is 1 and $R^1$ is a hydrogen atom, a hydroxyl group, a sulphydryl group, or a methoxy group.

4. The amide according to claim 3 which is N-[(3α,5β,7β)-3,7-dihydroxy-24-oxocholan-24-yl]-L-proline.

5. The amide according to claim 3 which is the N-[(3α,5β,7β)-3,7-dihydroxy-24-oxocholan-24-yl]-4-(trans)-hydroxy-L-proline.

6. The amide according to claim 3 which is N-[(3α,5β,7β)-3,7-dihydroxy-24-oxocholan-24-yl]-4-(transmethoxy-L-proline.

7. The amide according to claim 3 which is N-[(3α,5β,7β)-3,7-dihydroxy-24-oxocholan-24-yl]-D-proline.

8. The amide according to claim 3 which is the N-[(3α,5β,7β)-3,7-dihydroxy-24-oxocholan-24-yl]-D,L-proline.

9. The amide according to claim 3 which is N-[(3α,5β,6α,7α)-3,6,7-trihydroxy-24-oxocholan-24-yl]-L-proline.

10. The amide according to claim 3 which is N-[(3α,5β,6α)-3,6-dihydroxy-24-oxocholan-24-yl]-L-proline.

11. The amide according to claim 3 which is N-[(3α,5β,7β)-3,7-dihydroxy-24-oxocholan-24-yl]-4-(cis)thiohydroxy-L-proline.

12. An optical isomer or racemate of the amide according to claim 1 wherein n is 2 and $R_1$ is hydrogen.

13. The amide according to claim 12 which is 2-carboxy-N-[(3α,5β,7β)-3,7-dihydroxy-24-oxocholan-24-yl]-D,L-piperidine.

14. A pharmaceutical composition for oral administration comprising 100 to 750 mgs of an amide according to claim 1.

15. The composition of claim 14 which is in the form of a tablet, a capsule, a sugar coated tablet, or a granulate.

* * * * *